(12) United States Patent
Tal et al.

(10) Patent No.: US 9,585,667 B2
(45) Date of Patent: Mar. 7, 2017

(54) SCLEROTHERAPY CATHETER WITH LUMEN HAVING WIRE ROTATED BY MOTOR AND SIMULTANEOUS WITHDRAWAL FROM VEIN

(75) Inventors: Michael G. Tal, Woodbridge, CT (US); John P. Marano, Jr., Madison, CT (US)

(73) Assignee: Vascular Insights LLC, Madison, CT (US)

( * ) Notice: Subject to any disclaimer, the term of this patent is extended or adjusted under 35 U.S.C. 154(b) by 0 days.

(21) Appl. No.: 13/194,253

(22) Filed: Jul. 29, 2011

(65) Prior Publication Data

US 2012/0130415 A1 May 24, 2012

Related U.S. Application Data

(60) Provisional application No. 61/413,895, filed on Nov. 15, 2010.

(51) Int. Cl.
*A61B 17/3207* (2006.01)
*A61B 17/12* (2006.01)

(52) U.S. Cl.
CPC .... *A61B 17/12013* (2013.01); *A61B 17/3207* (2013.01); *A61B 17/320758* (2013.01); *A61B 2017/320733* (2013.01)

(58) Field of Classification Search
CPC ............. A61B 17/22; A61B 17/00008; A61B 17/3207
USPC ...... 604/192, 506–507, 131, 164.01–164.13, 604/165.01–165.04, 528
See application file for complete search history.

(56) References Cited

U.S. PATENT DOCUMENTS

| | | | | |
|---|---|---|---|---|
| 1,740,174 A | * | 12/1929 | Ramsey | A61B 17/34 27/24.1 |
| 2,212,477 A | * | 8/1940 | Mayer | A61M 5/32 99/532 |
| 3,405,712 A | * | 10/1968 | Pierick | A61M 5/284 604/88 |
| 3,530,492 A | * | 9/1970 | Ferber | A61M 5/32 604/117 |

(Continued)

FOREIGN PATENT DOCUMENTS

| | | |
|---|---|---|
| CA | 2405273 | 4/2001 |
| CN | 2148536 | 12/1993 |

(Continued)

OTHER PUBLICATIONS

International Search Report and Written Opinion dated May 23, 2012 for PCT Application No. PCT/US2011/060859.

(Continued)

*Primary Examiner* — Kami A Bosworth
*Assistant Examiner* — Matthew A Engel
(74) *Attorney, Agent, or Firm* — Baker & Hostetler LLP

(57) ABSTRACT

An apparatus for performing a vascular treatment. In some embodiments, the apparatus comprises a vascular therapy device comprising a vascular treatment device and a feeder. The vascular treatment device can connect to a wire configured for use in vascular treatment. The vascular treatment device can rotate the wire. The feeder can be configured for controller the longitudinal translation of the wire. The feeder and the vascular treatment device can be independently or combinedly controlled.

22 Claims, 7 Drawing Sheets

(56) References Cited

U.S. PATENT DOCUMENTS

| | | | |
|---|---|---|---|
| 3,631,847 A * | 1/1972 | Hobbs, II | A61B 5/02755 600/432 |
| 3,633,566 A * | 1/1972 | Grabhorn | A61B 5/1427 600/575 |
| 3,788,326 A * | 1/1974 | Jacobs | A61M 16/00 128/207.15 |
| 4,278,085 A * | 7/1981 | Shim | A61M 5/14232 128/DIG. 12 |
| 4,403,611 A * | 9/1983 | Babbitt | A61M 1/0023 604/118 |
| 4,577,514 A * | 3/1986 | Bradley | G01N 33/491 422/424 |
| 4,586,921 A * | 5/1986 | Berson | A61M 19/00 604/512 |
| 4,728,319 A | 3/1988 | Masch | |
| 4,791,937 A * | 12/1988 | Wang | A61B 10/0283 600/565 |
| 4,854,325 A * | 8/1989 | Stevens | A61B 17/22012 600/434 |
| 4,867,156 A | 9/1989 | Stack et al. | |
| 4,876,109 A | 10/1989 | Mayer et al. | |
| 4,906,236 A | 3/1990 | Alberts et al. | |
| 4,936,845 A * | 6/1990 | Stevens | A61B 17/320758 604/22 |
| 5,022,399 A | 6/1991 | Biegeleisen | |
| 5,047,013 A | 9/1991 | Rossdeutscher | |
| 5,074,871 A | 12/1991 | Groshong | |
| 5,087,244 A | 2/1992 | Wolinsky et al. | |
| 5,087,265 A | 2/1992 | Summers | |
| 5,100,425 A * | 3/1992 | Fischell et al. | 606/159 |
| 5,135,517 A | 8/1992 | McCoy | |
| 5,176,646 A * | 1/1993 | Kuroda | A61M 5/1456 128/DIG. 1 |
| 5,269,794 A | 12/1993 | Rexroth | |
| 5,330,481 A * | 7/1994 | Hood | F16L 37/2445 128/898 |
| 5,370,653 A | 12/1994 | Cragg | |
| 5,415,636 A | 5/1995 | Forman | |
| 5,449,351 A * | 9/1995 | Zohmann | A61M 25/06 604/158 |
| 5,549,601 A * | 8/1996 | McIntyre | A61B 18/24 600/108 |
| 5,578,014 A * | 11/1996 | Erez | A61B 5/1411 604/192 |
| 5,611,357 A | 3/1997 | Suval | |
| 5,628,730 A | 5/1997 | Shapland et al. | |
| 5,632,755 A | 5/1997 | Nordgren et al. | |
| 5,675,228 A | 10/1997 | O'Bryan | |
| 5,707,355 A * | 1/1998 | Zimmon | A61B 17/12036 604/104 |
| 5,709,657 A | 1/1998 | Zimmon | |
| 5,716,366 A | 2/1998 | Yates | |
| 5,766,191 A | 6/1998 | Trerotola | |
| 5,776,153 A * | 7/1998 | Rees | A61B 17/22 606/159 |
| 5,836,905 A | 11/1998 | Lemelson et al. | |
| 5,882,329 A | 3/1999 | Patterson et al. | |
| 5,893,858 A | 4/1999 | Spitz | |
| 5,902,266 A | 5/1999 | Leone et al. | |
| 5,908,395 A * | 6/1999 | Stalker | A61M 25/09041 600/585 |
| 5,911,700 A | 6/1999 | Mozsary et al. | |
| 5,921,963 A * | 7/1999 | Erez | A61B 5/1411 604/192 |
| 5,976,164 A | 11/1999 | Bencini et al. | |
| 6,048,332 A | 4/2000 | Duffy et al. | |
| 6,090,118 A | 7/2000 | McGuckin, Jr. | |
| 6,159,196 A | 12/2000 | Ruiz | |
| 6,165,187 A | 12/2000 | Reger | |
| 6,171,234 B1 | 1/2001 | White et al. | |
| 6,193,735 B1 * | 2/2001 | Stevens | A61B 17/320758 600/585 |
| 6,193,736 B1 * | 2/2001 | Webler | A61B 8/12 600/463 |
| 6,231,518 B1 | 5/2001 | Grabek et al. | |
| 6,258,087 B1 | 7/2001 | Edwards et al. | |
| 6,261,272 B1 * | 7/2001 | Gross | A61M 5/3291 604/272 |
| 6,273,882 B1 | 8/2001 | Whittier et al. | |
| 6,290,675 B1 | 9/2001 | Vujanic et al. | |
| D450,843 S | 11/2001 | McGuckin, Jr. et al. | |
| 6,346,095 B1 * | 2/2002 | Gross | A61M 5/3291 604/272 |
| 6,369,039 B1 | 4/2002 | Palasis et al. | |
| 6,402,745 B1 | 6/2002 | Wilk | |
| 6,443,929 B1 * | 9/2002 | Kuracina | A61B 5/150572 604/192 |
| 6,482,215 B1 | 11/2002 | Shiber | |
| 6,484,727 B1 | 11/2002 | Vaska et al. | |
| 6,517,528 B1 | 2/2003 | Pantages et al. | |
| 6,520,928 B1 * | 2/2003 | Junior | A61M 5/14546 604/152 |
| 6,544,221 B1 | 4/2003 | Kokish et al. | |
| 6,547,776 B1 * | 4/2003 | Gaiser | A61M 29/02 604/103.02 |
| 6,575,932 B1 * | 6/2003 | O'Brien | A61M 25/007 604/101.01 |
| 6,602,264 B1 | 8/2003 | McGuckin, Jr. | |
| 6,639,212 B1 * | 10/2003 | Guevremont | B01D 59/46 250/281 |
| 6,673,025 B1 | 1/2004 | Richardson et al. | |
| 6,679,886 B2 | 1/2004 | Weikel et al. | |
| 6,733,473 B1 | 5/2004 | Reifart et al. | |
| 6,824,550 B1 | 11/2004 | Noriega et al. | |
| 6,824,551 B2 * | 11/2004 | Trerotola | A61B 17/221 606/159 |
| 6,852,118 B2 | 2/2005 | Shturman et al. | |
| 7,025,774 B2 | 4/2006 | Freeman et al. | |
| 7,083,643 B2 | 8/2006 | Whalen et al. | |
| 7,108,704 B2 | 9/2006 | Trerotola | |
| 7,211,073 B2 | 5/2007 | Fitzgerald et al. | |
| 7,285,126 B2 | 10/2007 | Sepetka et al. | |
| 7,402,155 B2 * | 7/2008 | Palasis | A61B 17/32037 604/264 |
| 7,419,482 B2 * | 9/2008 | Nash | A61B 17/32037 128/898 |
| 7,670,328 B2 * | 3/2010 | Miller | A61B 10/025 604/187 |
| 7,713,231 B2 * | 5/2010 | Wulfman | A61B 5/061 604/93.01 |
| 7,862,575 B2 * | 1/2011 | Tal | A61B 17/00008 128/898 |
| 7,967,834 B2 * | 6/2011 | Tal | A61B 17/320758 606/159 |
| 8,029,491 B2 * | 10/2011 | Aboul-Hosn | A61M 1/367 604/28 |
| 8,038,664 B2 * | 10/2011 | Miller | A61B 17/32002 604/506 |
| 8,052,645 B2 * | 11/2011 | Slate | A61M 5/20 604/131 |
| 8,696,645 B2 | 4/2014 | Tal et al. | |
| 2001/0004700 A1 | 6/2001 | Honeycutt et al. | |
| 2002/0010418 A1 | 1/2002 | Lary et al. | |
| 2002/0072704 A1 | 6/2002 | Mansouri-Ruiz | |
| 2002/0077589 A1 * | 6/2002 | Tessari | A61K 9/122 604/82 |
| 2002/0077594 A1 | 6/2002 | Chien et al. | |
| 2002/0173812 A1 | 11/2002 | McGuckin et al. | |
| 2002/0188276 A1 | 12/2002 | Evans et al. | |
| 2003/0004568 A1 | 1/2003 | Ken et al. | |
| 2003/0045860 A1 | 3/2003 | Leu | |
| 2003/0120256 A1 | 6/2003 | Lary et al. | |
| 2004/0092967 A1 | 5/2004 | Sancoff et al. | |
| 2004/0147934 A1 | 7/2004 | Kiester | |
| 2004/0220519 A1 * | 11/2004 | Wulfman | A61B 5/061 604/93.01 |
| 2004/0254566 A1 * | 12/2004 | Plicchi | A61B 34/37 606/1 |
| 2005/0055040 A1 | 3/2005 | Tal | |

(56) References Cited

U.S. PATENT DOCUMENTS

| | | | |
|---|---|---|---|
| 2005/0055041 A1* | 3/2005 | Woods .................... | A61F 9/013 606/166 |
| 2005/0096642 A1* | 5/2005 | Appling ................. | A61B 18/24 606/15 |
| 2005/0165354 A1* | 7/2005 | Schwartz .............. | A61M 5/158 604/152 |
| 2006/0015169 A1 | 1/2006 | Letort | |
| 2006/0095015 A1* | 5/2006 | Hobbs .................. | A61B 18/245 604/508 |
| 2006/0106407 A1 | 5/2006 | McGuckin, Jr. et al. | |
| 2006/0217692 A1* | 9/2006 | Neuberger ............. | A61B 18/24 606/12 |
| 2006/0224110 A1* | 10/2006 | Scott ....................... | A61M 1/10 604/95.01 |
| 2007/0112308 A1* | 5/2007 | Kay .................... | B01F 3/04446 604/187 |
| 2007/0239140 A1 | 10/2007 | Chechelski et al. | |
| 2007/0282359 A1* | 12/2007 | Tal ................... | A61B 17/00008 606/159 |
| 2008/0009791 A1* | 1/2008 | Cohen ............... | A61M 25/0105 604/95.01 |
| 2008/0033458 A1* | 2/2008 | McLean ............. | A61B 17/0401 606/144 |
| 2008/0097224 A1* | 4/2008 | Murphy ............... | A61B 5/0066 600/478 |
| 2008/0108971 A1* | 5/2008 | Klein .................... | A61M 5/158 604/512 |
| 2008/0172012 A1* | 7/2008 | Hiniduma-Lokuge .. | B21G 1/08 604/272 |
| 2008/0243068 A1 | 10/2008 | Ramzipoor et al. | |
| 2008/0300571 A1* | 12/2008 | LePivert ............ | A61B 18/1492 604/503 |
| 2008/0300574 A1* | 12/2008 | Belson .............. | A61M 25/0606 604/510 |
| 2009/0137906 A1* | 5/2009 | Maruyama ........... | A61B 5/1422 600/461 |
| 2009/0222003 A1* | 9/2009 | Otley ..................... | A61B 17/12 606/41 |
| 2009/0270888 A1 | 10/2009 | Patel et al. | |
| 2009/0270889 A1 | 10/2009 | Tal et al. | |
| 2010/0069760 A1* | 3/2010 | Tang .................. | A61B 5/02007 600/478 |
| 2010/0125276 A1 | 5/2010 | Palermo | |
| 2010/0268076 A1* | 10/2010 | Gat ..................... | A61M 25/007 600/435 |
| 2010/0274178 A1* | 10/2010 | LePivert ................ | A61B 18/02 604/21 |
| 2011/0015484 A1* | 1/2011 | Alvarez ................. | A61B 1/307 600/109 |
| 2011/0066142 A1* | 3/2011 | Tal ................. | A61B 17/320758 606/1 |
| 2012/0130410 A1 | 5/2012 | Tal et al. | |
| 2012/0130411 A1* | 5/2012 | Tal ................... | A61B 17/12013 606/159 |
| 2012/0197200 A1* | 8/2012 | Belson .............. | A61M 25/0606 604/164.12 |
| 2012/0265168 A1* | 10/2012 | Horowitz ........... | A61B 17/3401 604/512 |
| 2014/0200599 A1* | 7/2014 | Shiber ............ | A61B 17/320758 606/159 |
| 2014/0207052 A1 | 7/2014 | Tal et al. | |

FOREIGN PATENT DOCUMENTS

| | | |
|---|---|---|
| DE | 10059742 | 6/2002 |
| EP | 0501081 | 9/1992 |
| FR | 2651682 | 3/1991 |
| JP | 2002-506670 A | 3/2002 |
| JP | 2003-523803 | 8/2003 |
| JP | 2003/299662 | 10/2003 |
| JP | 2007-301392 A | 11/2007 |
| JP | 2008-520351 A | 6/2008 |
| JP | 2009/078150 | 4/2009 |
| JP | 2009-078150 A | 4/2009 |
| JP | 2009-254874 A | 11/2009 |
| JP | 2010-503479 A | 2/2010 |
| JP | 2011-512983 A | 4/2011 |
| WO | WO 97/14362 | 4/1997 |
| WO | WO 98/12967 A1 | 4/1998 |
| WO | WO 99/04701 A1 | 2/1999 |
| WO | WO 99/47056 A1 | 9/1999 |
| WO | WO 01/54754 A1 | 8/2001 |
| WO | WO2008005888 A2 | 1/2008 |
| WO | WO 2008/033983 A1 * | 3/2008 |
| WO | WO 2009/109967 | 9/2009 |
| WO | WO 2012/068162 | 5/2012 |
| WO | WO 2012/068165 | 5/2012 |
| WO | WO 2012/068166 | 5/2012 |

OTHER PUBLICATIONS

International Search Report and Written Opinion dated May 30, 2012 for PCT Application No. PCT/US2011/060860.

International Search Report and Written Opinion dated May 30, 2012 for PCT Application No. PCT/US2011/060855.

International Search Report dated Jan. 11, 2008 for PCT Application No. PCT/US2007/078367.

Written Opinion dated Jan. 11, 2008 for PCT Application No. PCT/US2007/078367.

Williams et al. "Sclerosant Treatment of Varicose Veins and Deep Vein Thrombosis," Archives of Surgery, vol. 119, No. 11, Nov. 1984.

International Search Report dated Nov. 2, 2005 for PCT Application No. PCT/US04/15858.

Written Opinion dated Nov. 2, 2005 for PCT Application No. PCT/US04/15858.

International Preliminary Report on Patentability dated Jun. 5, 2013 for PCT Application No. PCT/US2011/060855.

International Preliminary Report on Patentability dated May 16, 2013 for PCT Application No. PCT/US2011/060859.

\* cited by examiner

SCLEROTHERAPY CATHETER WITH LUMEN HAVING WIRE ROTATED BY MOTOR AND SIMULTANEOUS WITHDRAWAL FROM VEIN

CROSS-REFERENCE TO RELATED APPLICATIONS

This application claims the benefit of U.S. Provisional Application No. 61/413,895, filed on Nov. 15, 2010.

BACKGROUND OF THE INVENTION

Field of the Invention

This specification relates to the field of vascular treatment.

Description of the Related Art

Sclerotherapy can be used to treat blood vessels, blood vessel malformations, and similar problems in other body systems, such as the lymphatic system, and has been used in various forms for over 150 years. In its more modern form, sclerotherapy has been used since the 1960's, in Europe, for treating various vein conditions such as; varicose veins, reticular veins, spider veins of the leg, and also some fine facial veins.

Sclerotherapy can be used to treat these conditions by instigating vascular fibrosis and obliteration in response to irreversible endothelial cellular destruction and exposure of the underlying subendothelial cell layer. This destruction is usually caused by the injection of a sclerosant into the vein. However, if the injected sclerosant is too weak, there may be no endothelial injury at all. If the sclerosant is a little stronger, the varicose vessel is damaged, but recanalization occurs and an incompetent pathway for retrograde blood flow persists. Finally, if the injected sclerosant is too strong, the varicose vessel endothelium is destroyed, but adjacent vessels that are not targeted for treatment may also be damaged by the sclerosant.

The requirement for an ideal strength of the sclerosant is complicated by the constant flow of blood through the vein that is being treated. This flow simultaneously dilutes, and thereby weakens, the sclerosant, while also transporting the sclerosant to other parts of the vascular system.

Thus, improved methods and devices for treating the vascular system are desired.

SUMMARY OF THE INVENTION

In some embodiments, an apparatus can be configured for permanently occluding a vein. The apparatus can have an elongated intraluminal member shaped and dimensioned for passage through blood vessels of a subject. The intraluminal member can include a proximal end and a distal end. The distal end can also include a vein wall disruptor. An apparatus can further have a source of sclerosant. An apparatus can also have a fluid channel between the source of sclerosant and the distal end of the elongated intraluminal member. An apparatus can further include a first motor coupled to the intraluminal member to move the intraluminal member in a manner providing local vein damage. An apparatus can further include a second motor coupled to the intraluminal member to withdraw the intraluminal member.

The second motor may be able to withdraw the intraluminal member at variable rates. For example, the second motor can increase the rate of withdrawal of the intraluminal member during the procedure. In some embodiments, the second motor is configured to withdraw the intraluminal member at a rate of approximately 1-4 mm per second.

The apparatus can be used for permanently occluding a vein through the combined disruption of a vein vessel wall and application of a sclerosant. The apparatus can be used to advance an elongated intraluminal member from an access site and into the vein. The intraluminal member can have a portion that damages the inner vessel wall of the vein and is controlled by the user when performing a defined movement. The apparatus can damage the inner vessel wall moving the portion of the intraluminal member against the vein's endothelium in the defined motion while simultaneously withdrawing the intraluminal member with a motor. The apparatus can further inject sclerosant into the vein and onto the damaged inner vessel wall.

In some embodiments, the motor can withdraw the intraluminal member at a non-constant rate during the damaging. In some embodiments, the motor can increase the rate of withdrawal of the intraluminal member during the damaging. In some further embodiments, the motor can decrease the rate of withdrawal of the intraluminal member during the damaging. In some further embodiments, the motor can withdraw the intraluminal member at a rate of approximately 1-4 mm per second.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

DETAILED DESCRIPTION

The following description and examples illustrate preferred embodiments in detail. Those of skill in the art will recognize that there are numerous variations and modifications of this invention that are encompassed by its scope. Accordingly, the description of a preferred embodiment should not be deemed to limit the scope of the present invention. In this description, reference is made to the drawings wherein like parts are designated with like numerals throughout.

Figure 1:
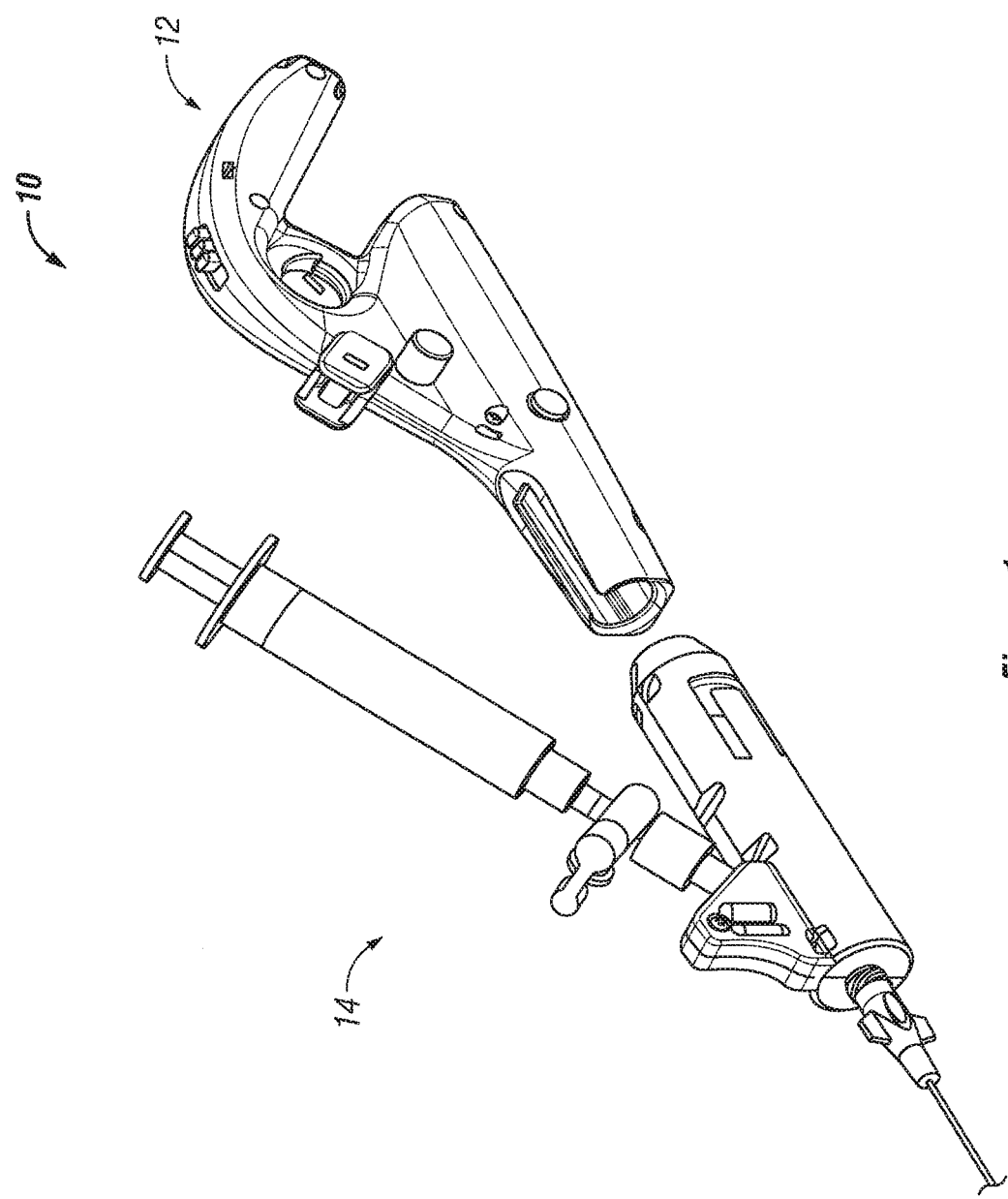
FIG. 1 shows an embodiment of an assembly of a vascular treatment device.

FIG. 1 depicts a perspective view of one embodiment of exemplary components of a vascular treatment device 10. These components can be configured to provide a range of functionalities to the vascular treatment device 10. In some embodiments, a vascular treatment device 10 can include features configured for stimulating vascular ablation, such as, for example, a wire, motor, and/or control features and/or features configured for delivering liquid, such as, for example, a sheath or a catheter. As depicted in FIG. 1, a vascular treatment device can include a handle 12 and a cartridge 14. As explained below in greater detail, each of the handle and cartridge can include features configured for stimulating vascular ablation and/or for delivering liquid. In one embodiment, and as depicted in FIG. 1, the handle 12 and the cartridge 14 can comprise separate pieces. In another embodiment, a handle 12 and a cartridge 14 can comprise an integrated component. A person of skill in the art will recognize that the present disclosure is not limited to a specific configuration of the handle 12 and cartridge 14 but broadly includes the range of functions and uses of a vascular therapy device.

As further depicted in FIG. 1, the cartridge 14 can be, for example, sized and shaped to engagingly connect to the handle 12. In one embodiment, and as shown in FIG. 1, this engaging connection can be achieved by fitting features of the handle 12 to features of the cartridge 14.

Figure 2:
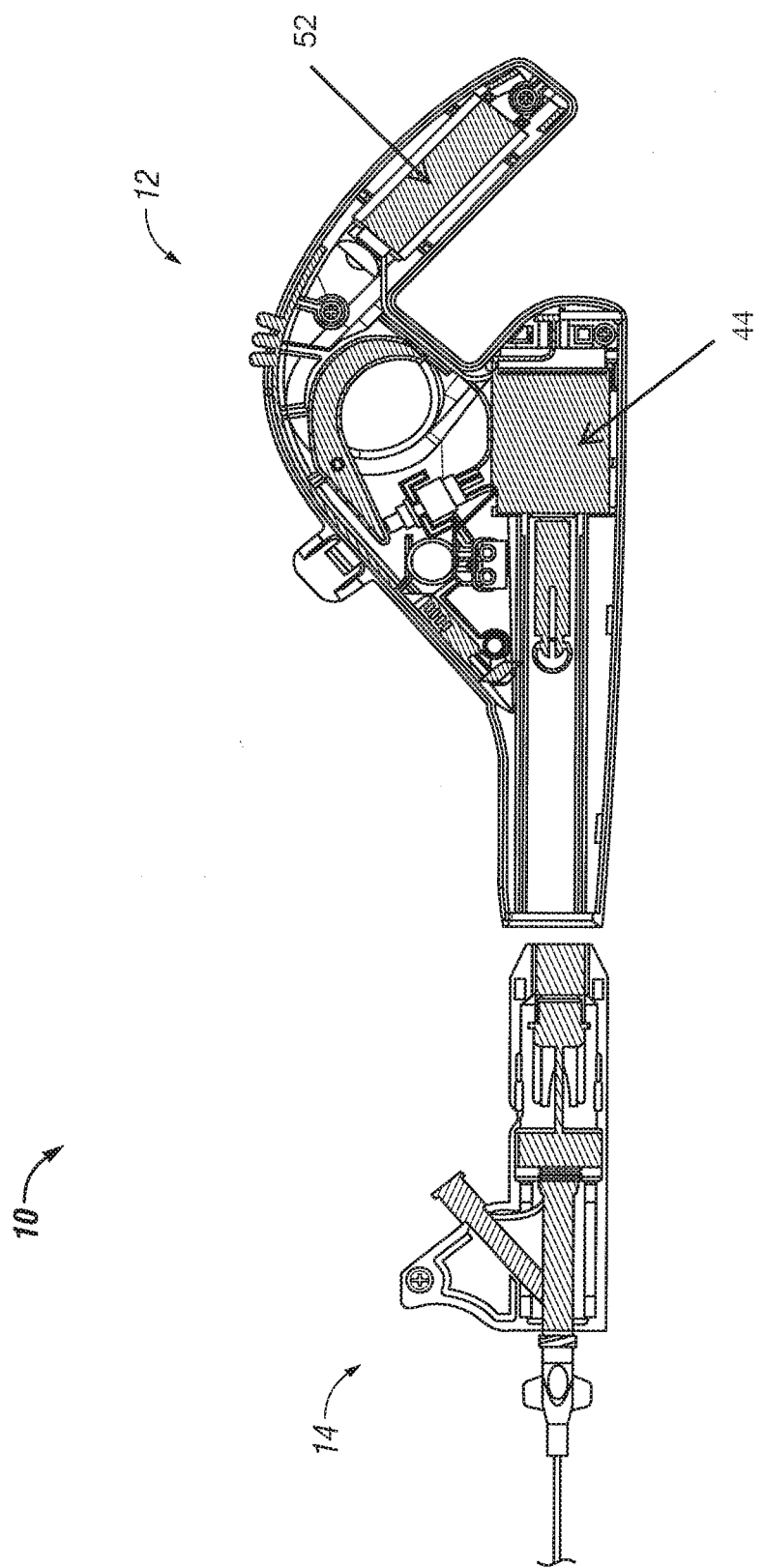
FIG. 2 illustrates a longitudinal cross-sectional view of the embodiment illustrated in FIG. 1.

FIG. 2 depicts a side cross-section view of a similar embodiment of a vascular treatment device 10 having a handle 12 and a cartridge 14. The vascular treatment device 10 depicted in FIG. 2 comprises the same features discussed in relation to FIG. 1. A person of skill in the art will recognize that the present disclosure is not limited to embodiments of a vascular treatment device 10 comprising a handle 12 and a cartridge 14, but broadly encompasses the functionality of a vascular treatment device 10 as described below.

Figure 3:
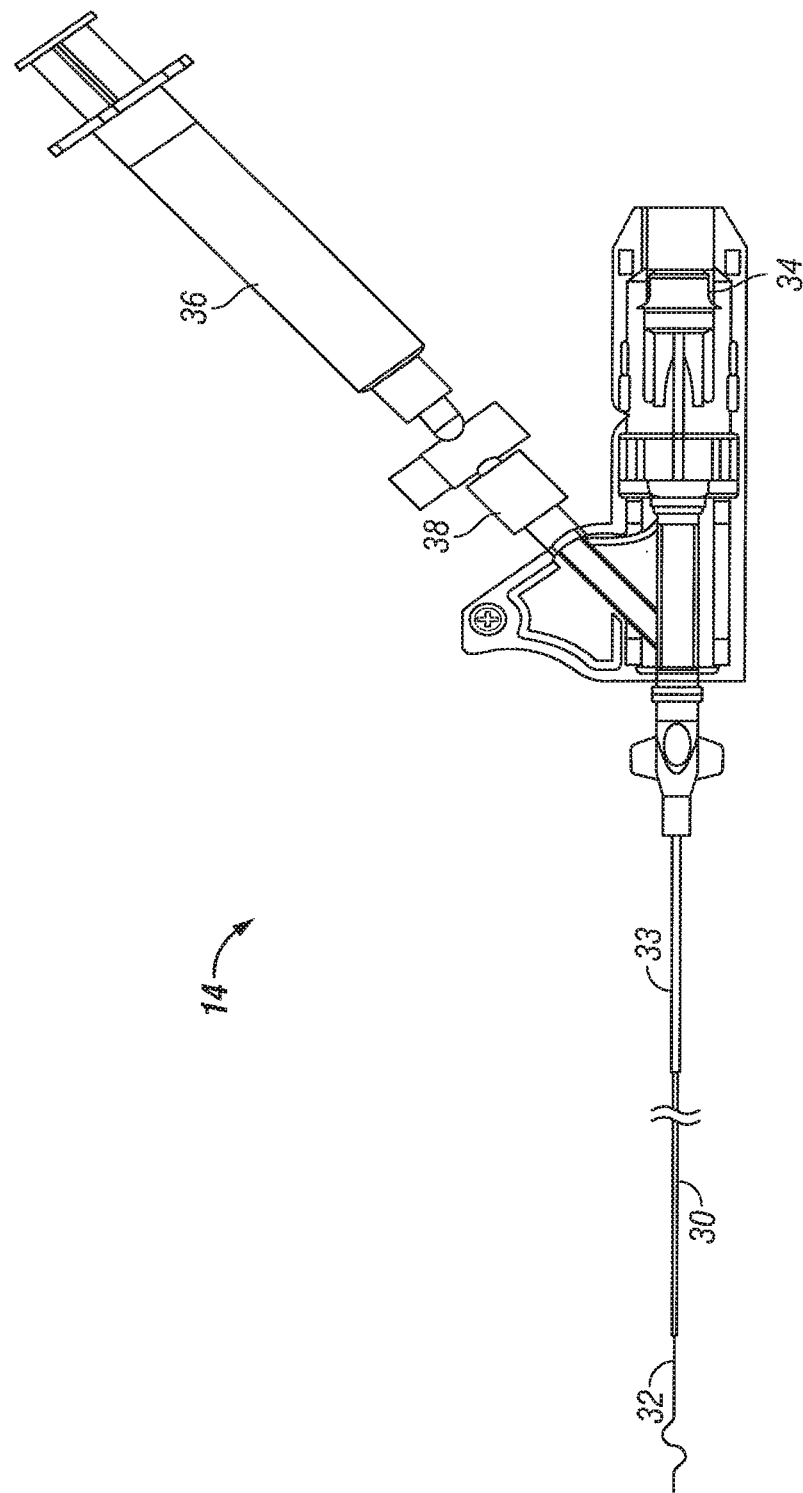
FIG. 3 shows a longitudinal cross-section view of a cartridge with a syringe and a stopcock attached.

The embodiment of cartridge 14 shown in FIGS. 1 and 2 is illustrated in greater detail in FIG. 3. A vascular treatment device 10 can include an intraluminal member. In some embodiments, an intraluminal member can comprise a wire. In some embodiments, an intraluminal member can comprise a sheath surrounding the wire.

The cartridge 14 depicted in FIG. 3 includes a sheath 30 affixed to and extending from the cartridge 14, a wire 32, and a coupling 34. In some embodiments, the wire 32 can be, for example, fixed to the coupling 34. A person of skill in the art will recognize that the wire 32 can be affixed to the coupling 34 through a variety of techniques and methods. A person of skill in the art will further recognize that the wire 32 can be affixed to a range of features of a vascular treatment device 10 configured for driving the wire 32. A strain relief tube 33 can be provided where the sheath and wire exit the cartridge 14.

A wire 32 can comprise a variety of materials and geometric configurations. In some embodiments, a wire 32 can be configured to facilitate injection of liquid into a patient. For example, a wire 32 can be annular or channeled to allow fluid flow to the desired injection point. Similarly, a sheath 30 can comprise a variety of materials and geometric configurations, and can, in some embodiments, be configured to facilitate injection of liquid into a patient. For example, an annular sheath 30 configured for containing a wire can be further configured to allow injection of liquid through the annular passage around the wire 32.

A wire 32 can comprise a variety of lengths. In some embodiments, a wire 32 can have a length matching the needs of the procedure. In some embodiments, a wire 32 can have a length, for example, of up to 10 cm, up to 25 cm, up to 75 cm, or up to 150 cm.

The wire tip located on the distal end may have a wide variety of configurations, depending on the intended use. The wire shape may be "atraumatic," meaning that it may be shaped such that insertion causes little or no spasm or damage to the vessel. For example, the distal end may terminate with a hemispheric free end. The hemispheric end may be textured or mechanically or chemically altered to create a roughened surface. Other atraumatic tips may include an end having a full radius, or a J-curved shape, or simply a curved shape.

In other embodiments, the distal tip may be "aggressive" and be bent or curved so that it scrapes the vessel wall. The distal end may have a flat free end with a sharp edge around. An aggressive distal tip may also be created by beveling an edge to create a sharp point. The distal tip having a cutting blade, like a shark's fin, may also be aggressive. The distal tip may be roughened to make the distal tip cut more aggressively and/or cause spasm to the blood vessel wall.

In general, the disruption and/or irritation is caused by a mechanical device, which when positioned in the vessel provides an outwardly directed radial force to engage, irritate and damage but not break through the inner vessel wall.

The sheath 30 can, in some embodiments, be configured to define a lumen through which the wire 32 runs. In some embodiments, the sheath can be configured to allow independent motion of the wire within the sheath. The sheath 30 can have a variety of inner and outer diameters. In some embodiments, the sheath 30 can have an inner diameter ranging from approximately 0.022 inches to 0.048 inches. In some embodiments, the sheath 30 can have an outer diameter ranging from approximately 0.025 inches to 0.051 inches. In some embodiments, the outer diameter of the sheath 30 can be in the range that is, for example, consistent with the inner diameter of standard needles. In one embodiment, for example, the sheath 30 can be sized and shaped to be insertable in a standard needle or vascular sheath having, for example, an inner diameter ranging from approximately 0.0035 inches to 0.0160 inches, from approximately 0.0160 inches to 0.0420 inches, from approximately 0.0420 inches to 0.0630 inches, or from approximately 0.0115 inches to 0.0630 inches.

In some embodiments, for example, the sheath 30 can be dimension to be insertable through a needle diameter that is sufficiently small to enable a wide variety of practitioners to perform the procedure. Thus, in one embodiment, the maximum outer diameter of the sheath 30 can be, for example, less than 0.035 inches to allow the sheath 30 to be inserted through an intravenous needle or catheter having an inner diameter of less than 0.0039 inches, which needle size is sufficiently small to allow a wide range of practitioners to perform the procedure.

The sheath 30 may also include external markings at regular intervals which may guide the user to monitor the insertion or removal speed of the device 10.

Some embodiments of a vascular treatment device 10 can be configured for use with injectant. In some embodiments, the cartridge 14 can be configured for holding an injectant. Some embodiments of a vascular treatment device configured to inject an injectant can include a container for storing an injectant and injection features, such as, for example, a pump or a syringe. In some embodiments of a cartridge 14, a syringe 36 can fluidly connect with the cartridge 14. Some embodiments of a vascular treatment device 10 and/or a cartridge 14 configured for use in connection with an injectant can be, for example, configured with valves and connectors to facilitate such use. In some embodiments, a syringe 36 can, for example, connect to a stopcock 38 on a cartridge 14. The stopcock 38 shown in FIG. 3 can be configured to allow the removal and/or attachment of a syringe to the vascular treatment device 10 during a procedure. In some embodiments, a stopcock 38 can be configured to allow reloading of fluid and/or exchanging of containers to, for example, change the injectant or the concentration of the injectant. In some embodiments, the stopcock 38 can be configured to provide additional functionality, such as, for example, mixing or aerating the injectant.

Figure 4:
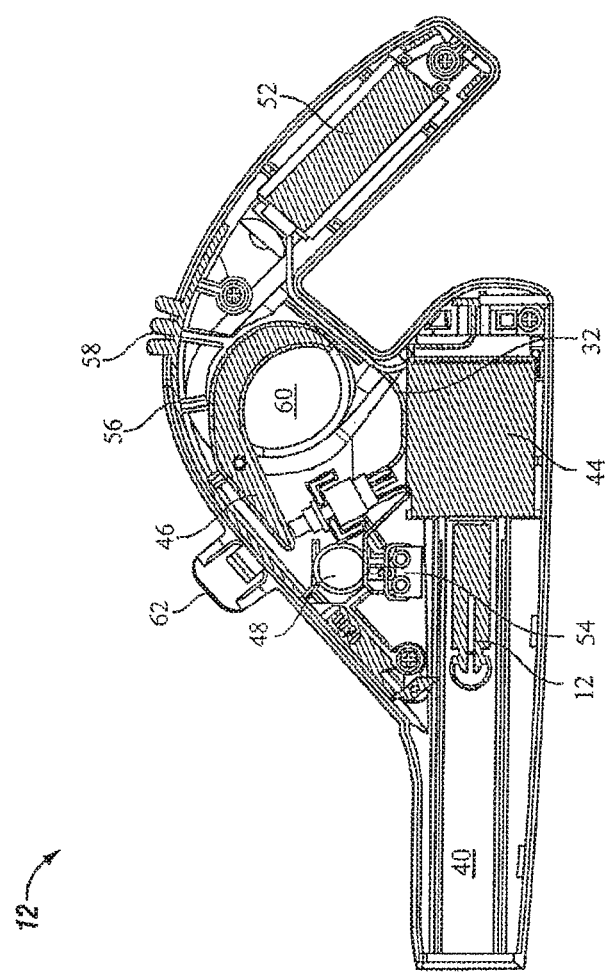
FIG. 4 shows a longitudinal cross-sectional view of a handle.

FIG. 4 depicts a side cross-section view of one exemplary embodiment of the handle 12. The handle 12 can be, for example, formed of one or several pieces. Additionally, the handle 12 can be formed using a variety of techniques and from a variety of materials, such as, for example, natural materials, synthetic materials, metal, polymer, glass, composites, or any combination thereof. In some embodiments, the handle 12 can be, for example, formed by joining two outer casing pieces.

In some embodiments in which the handle 12 is separate from the cartridge 14, the handle 12 can define a receptacle 40 configured to receive the cartridge 14. As depicted in FIG. 4, the receptacle 40 can, for example, include a male coupling 42 that can be, for example, configured and positioned to receive female coupling 34 of the cartridge 14 when the cartridge 14 and the handle 12 engage. In some embodiments, the handle 12 can, for example, include at least one motor 44. The exemplary embodiment of a handle 12 depicted in FIG. 4 includes a motor 44, a trigger 46, and a male coupling 42. As also depicted in FIG. 4, in some embodiments, the male coupling 42 can be drivably connected to the motor 44 such that the motor 44, when activated, drives the male coupling 42.

A vascular treatment device 10 can be configured to control the movement of an intraluminal member. In some embodiments, a motor 44 can control the movement of the intraluminal member. In some embodiments, of a vascular treatment device 10, a motor 44 can rotably drive an intraluminal member, such as, for example, a wire 32.

In some embodiments, a potentiometer 48 can be electrically coupled to the motor 44 and can be configured to control the speed of the motor 44. In some embodiments, control features can control the motor 44. In some embodiments, the control features can mechanically, electrically, or communicatingly, e.g. wirelessly or via Bluetooth, connect with the vascular treatment device 10. In some embodiments, the control features can comprise a trigger 46. The trigger 46 can be, for example, mounted on the handle 12 and be transitionable between a first state in which the motor 44 is not electrically coupled to a power source 52, and a second state in which the motor 44 is electrically coupled to a power source 52.

In some embodiments of a vascular treatment device 10, and as discussed above, activation of the motor 44 can cause rotation of the wire 32. In some embodiments, a vascular treatment device 10 can be configured to generate a desired speed of wire 32 rotation. In some embodiments, for example, a motor 44 can be configured to rotate a wire 32 up to approximately 100 rpm, up to 500 rpm, up to 1,000 rpm, or up to 5,000 rpm. In some embodiments, in which a vascular treatment device 10 is configured for use in varicose vein and thrombectomy procedures the motor 44 can be configured for speeds of between 500 to 4,000 rpm. Some embodiments of a vascular treatment device 10 further comprise at least one feedback feature, such as, for example, a built-in RPM display. A person of skill in the art will recognize that a vascular treatment device 10 can be configured to generate a broad range of speeds of wire 32 rotation and that the present disclosure is not limited to any specific speed of rotation.

As depicted in FIG. 4, some embodiments of the handle 12 can include, for example, a power source 52 and a microswitch 54 connected to the motor 44. The microswitch 54 may be interposed in an electrical circuit connecting the trigger 46 and the motor 44. The microswitch 54 may be biased to an open position such that the circuit between the trigger 46 and the motor 44 is open. When the cartridge 14 is engaged in the handle 12, the cartridge may press against the microswitch 54, causing it to transition to a closed state, thereby completing the electrical circuit connecting the trigger 46 and motor 44. For example, the microswitch 54 may include two contacts with a conductor that is attached to one contact and disconnected from the second contact when the microswitch 54 is in an open state. In one embodiment, the conductor may include a strip of metal that hangs in the channel into which the cartridge 14 is slid during engagement with the handle. As the cartridge 14 is engaged in the handle 12, it pushes the metal strip out of the channel and into connection with the second contact of the microswitch 54. One advantage gained from such configuration may be that a user will not be able to activate the device inadvertently by pressing on the trigger 46 before he/she is ready to use the device, i.e., before the cartridge 14 is fully engaged to the handle 12.

In some embodiments in which the handle 12 and the cartridge 14 are separate components, the handle 12 can, for example, include a switch 56 as shown in FIG. 4. The switch 56 can, for example, be configured to allow the cartridge 14 to be received by, and secured in, the handle 12. The switch 56, in some embodiments, includes a grip 58 configured to permit a user to operate the switch 56 with a finger.

In some embodiments, one or more portions of the handle 12 can define a trigger ring 60 in which the trigger 46 is at least partly disposed and about which the handle 12 can be, for example, so arranged as to be balanced when supported from only one or more portions of the handle 12 that define the trigger ring 60. In some embodiments, the heaviest component can be, for example, positioned below the trigger 46. In some aspects, positioning of the heaviest component below the trigger 46 can assist in properly balancing the handle. In some embodiments, in which the motor 44 is, for example, the heaviest component, the motor 44 can be located below the trigger 46 as shown in FIG. 4.

The handle 12 can, for example, include features configured to facilitate in the storage and injection of liquid. In some embodiments, a handle 12 can include, for example, a support 62 positioned to receive the syringe. The support 62 can have a variety of sizes and shapes. In some embodiments, the support 62 can be sized and shaped to be compatible with a designated container, such as, for example, a standard syringe. The support 62 can, in further embodiments, be configured to prevent the container from falling out during injection. In some embodiments, the support 62 can be configured to connectingly engage the container. In one embodiment, for example, the syringe may snap onto the support 62 when the cartridge 14 with an attached syringe is engaged to the handle 12.

More detailed description of several of the above described components, and other components of embodiment of a vascular treatment device can be found in U.S. Publication No. 2005/0055040 and in U.S. Publication No. 2009/0270889, both of which are hereby incorporated by reference in their entireties. In general, the device pictured in FIGS. 1-4 is used to ablate blood vessels by feeding the wire and sheath into a vein to be ablated, and rotating or otherwise moving the tip of the wire against the vein to damage the endothelium of the inner vein wall. Before, during, or after this damaging process, sclerosant is injected into the vein through the sheath or wire as described above. The combined effect of the damage and the sclerosant results in a highly successful ablation procedure.

In performing these procedures, the physician usually initiates the scraping and vein damaging process with the wire, and at the same time slowly pulls the wire back down the vein toward the original access point to scrape along a large segment of the vein to be ablated. The speed of removal is typically several mm per second, with 1 to 4 mm per second having been found suitable. Maintaining a relatively constant removal rate manually has been found difficult however. The physician may wish to withdraw tens of centimeters of the wire at just a few millimeters per second. Additionally, the benefits achieved by controlling the amount of damage caused by the wire tip to the blood vessel wall is difficult to achieve when pulling the vascular treatment device by hand. This can occur because of the difficulty in maintaining a constant extraction speed over lengths of tens of centimeters.

In some embodiments, a vascular treatment device can include features to control the degree to which the wire tip engages with the blood vessel walls. A vascular treatment device 10 can, for example, be used in connection with a first motor 44 and a second motor 512. In some embodiments of a vascular treatment device 10 used in connection with a first motor 44 and a second motor 512, the first motor 44 can be configured to controllably rotate the wire 32. In some further embodiments of a vascular treatment device 10 having a first motor 44 and a second motor 512, the second motor 512 can be configured to control the longitudinal translation of the wire 32 back toward the access point. In some embodiments, the vascular treatment device 10 can include features configured to rotate the wire 32 at a predetermined speed and to simultaneously longitudinally translate the wire 32 at a predetermined speed. In some embodiments, the speed of the wire 32 rotation and longitudinal translation can be related to each other. In some embodiments, the speed of the wire 32 rotation and/or the longitudinal translation of the wire 32 can be varied throughout the vascular therapy procedure. In other embodiments, the speed of the wire 32 rotation and/or the longitudinal translation of the wire 32 can be varied in response to user control or to other information. In some embodiments, a feeder can comprise the second motor 512 that is configured to longitudinally translate the wire 32. A feeder can, in some embodiments, be configured to controllably longitudinally translate an intraluminal member. A person of skill in the art will also recognize that a feeder can be configured to provide for a variety of lengths of longitudinal translation of a wire. Some embodiments, for example, of a translation device can be configured to provide up to 50 cm, 75 cm, or over 100 cm of longitudinal translation. Some embodiments of a vascular therapy device, for example, can longitudinally translate a wire at speeds between 0 and up to about 20 mm per second. As mentioned above, a controllable speed of between 1 and 4 mm per second can be useful in many procedures.

Figure 5:
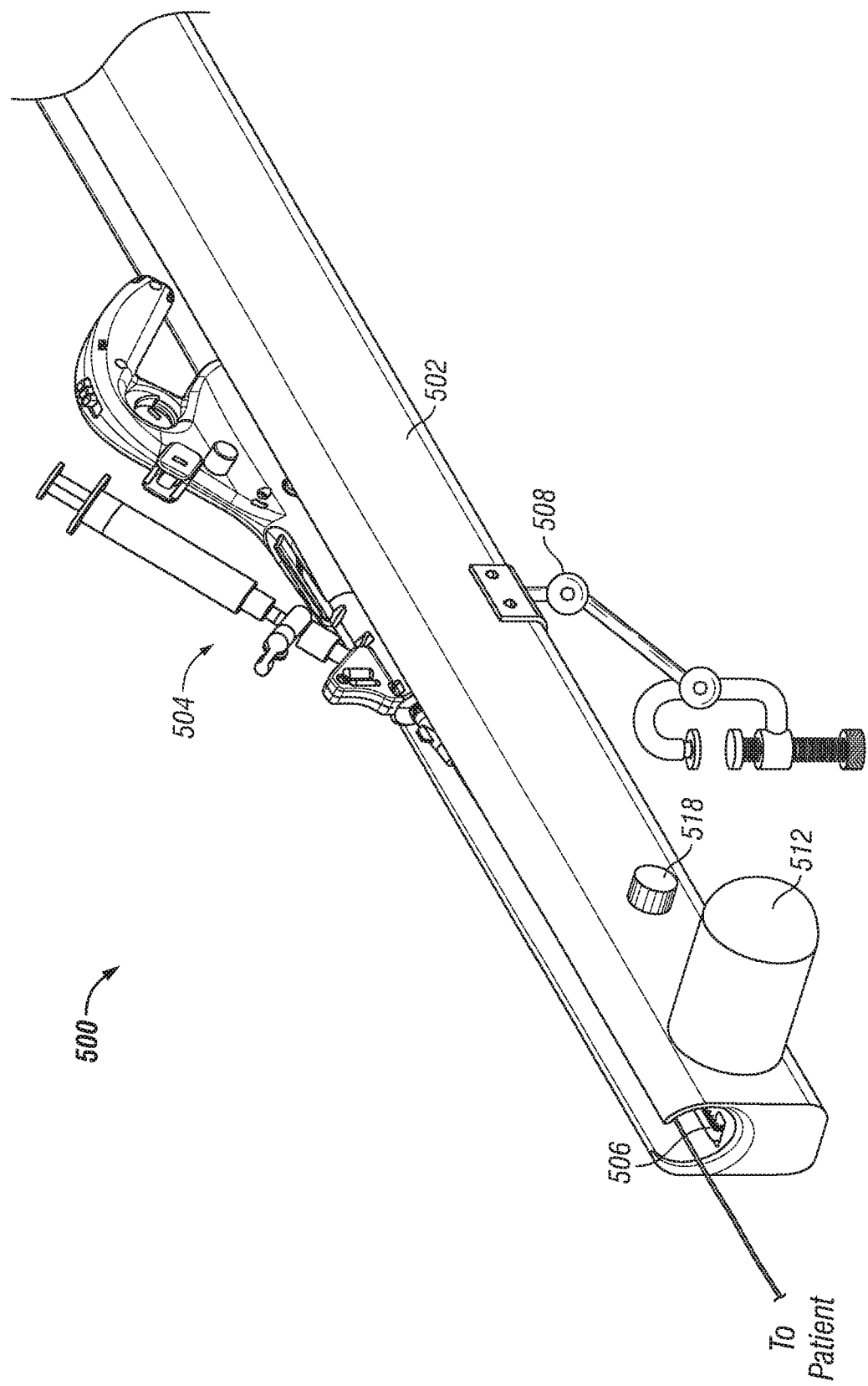
FIG. 5 shows a perspective view of an embodiment of a feeder used in connection with a vascular treatment device.

FIG. 5 depicts one embodiment of a vascular therapy apparatus configured to enable control of both the rate of wire rotation and longitudinal translation of the wire. FIG. 5 depicts a feeder 500 comprising an elongate track 502. The elongate track 502 can comprise a variety of shapes and dimensions. In the embodiment depicted in FIG. 5, the elongate track 502 comprises a U-shaped elongate member. The track 502 can be configured to hold the vascular treatment device 504 that is described above with reference to FIGS. 1-4. In some embodiments, a track 502 can be configured with features to facilitate longitudinal translation of the vascular treatment device 504 including, at least one roller, at least one bearing, at least one bushing, at least one air jet, at least one magnet, or other feature. FIG. 5 depicts one embodiment of a track 502 comprising a belt 506. The belt runs along the bottom of the elongate member, returning through a hollow bottom portion of the track 502. The belt 506 can include features for connecting the belt to the vascular treatment device 504. In some embodiments, these features can comprise loop and hook fasteners, magnets, clamps, adhesive strips, or other features. In one particular embodiment, the belt 506 can comprise either the hook or the loop portion of a hook and loop fastener. The portion of the hook and loop fastener associated with the belt 506 can be integrally formed with the belt or can be, for example, mechanically or adhesively affixed to the belt 506. The vascular treatment device 504 can be configured to comprise the other half of the hook and loop faster affixed on the bottom portion of the vascular treatment device 504 such that the half of the hook on loop fastener on the vascular treatment device 504 can be brought into contact with the half of the hook and loop fastener located on the belt 506.

FIG. 5 depicts one embodiment of a track 502 in which the belt 506 is driven by the second motor 512. The second motor 512 can be selected to match the power and speed requirements of a specific embodiment of a track 502 with a belt 506. A person of skill in the art will recognize that a variety of motors can be used in connection with the belt 506. The speed of the second motor 512 can be controlled with control features. FIG. 5 depicts one embodiment of a control feature 518. Which may be a potentiometer coupled to a motor control circuit inside the hollow bottom of the track 502. In this embodiment, controller 518 is located on the track 502. In other embodiments, the controller 518 can be separate from the track 502. The apparatus can additionally comprise a feedback feature, such as a display, that provides information to the operator relating to the operation of the feeder 500.

The embodiment of a feeder 500 comprising a track 502 can be free-standing or can be mounted to another object. In the embodiment depicted in FIG. 5, the feeder 500 is attached to an articulating arm 508. A person of skill in the art will recognize that an articulating arm can comprise a variety of components made of a variety of materials and assembled in a variety of ways. In some embodiments, and as depicted in FIG. 5, the articulating arm can include a include features for affixing the arm to an object. In some embodiments, these features can include, for example, a C-clamp. In one embodiment, a C-clamp is located at the end of an articulating arm and can be configured to allow fixation of the articulating arm to, for example, an operating table or a hospital bed.

During the procedure, the physician would hold the handle of the device 504, holding the trigger down to initiate wire rotation and vessel damage as described above. Before or after this has begun, second motor 512 can be started and adjusted to the desired speed with which the device should be pulled back along the track by the belt 506. It would be possible also to utilize a lever, button, or other control feature on the handle to allow hands free wire rotation as the device is also pulled back at the desired rate in the track.

Figure 6A:
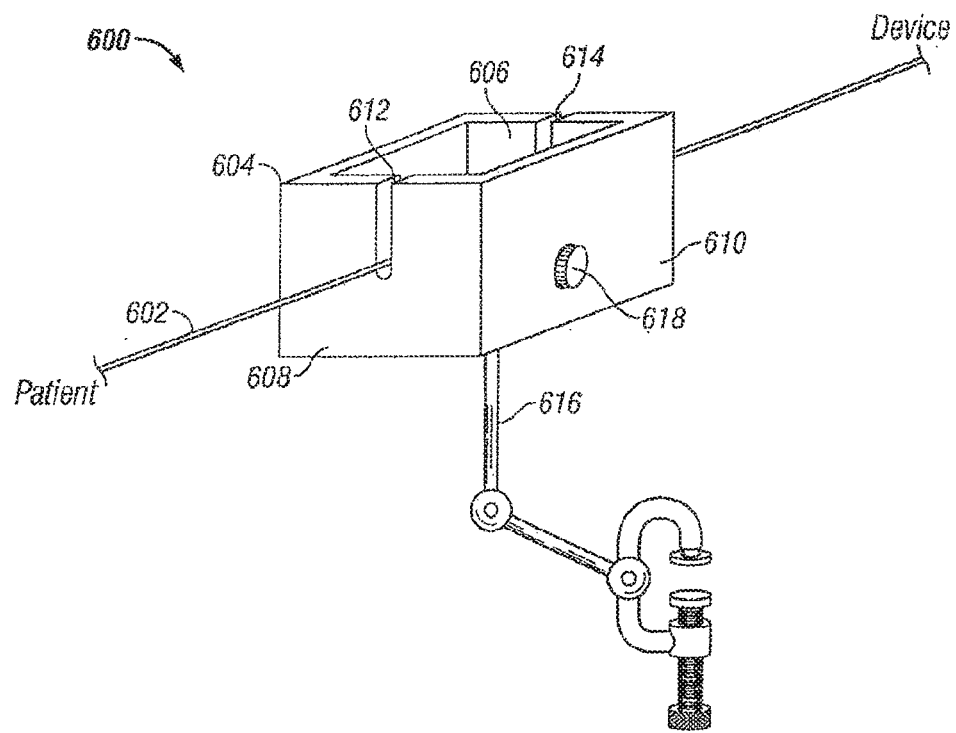
FIG. 6A shows a perspective view of one embodiment of a feeder.

FIG. 6A depicts one embodiment of a mechanism configured to control longitudinal translation of the wire in an automated manner. FIG. 6A depicts a feeder 600 configured to longitudinally translate a rotating wire or wire/sheath combination 602. The feeder 600 comprises a housing 604. The housing 604 can be made of a variety of materials such as, for example, natural materials, synthetic materials, polymer, metal, glass, composite, or any other material. A housing 604 can have a variety of shapes and sizes. The housing can cover a variety of components such as, for example, at least one motor, at least one gear, wiring, at least one roller, at least one bushing, at least one bearing, at least one antenna, at least one switch, at least one computer chip, at least one pump, or other components. The housing depicted in FIG. 6A has an open top 606, a bottom (not shown), a first face 608, which face is positioned relatively closest to the patient and allows the wire to pass into the feeder, a second face (not shown), which face is positioned relatively closest to the device and allows the wire to pass out of the feeder, a first side 610, and a second side (not shown). As depicted in FIG. 6A, the first face 608 can include a first slot 612 configured to allow the wire 602 to pass through the plane of the first face 608. Similarly, the second face can include a second slot 614 configured to allow the wire 602 to pass through the plane of the operator face. In some embodiments, the slots can be configured to allow the wire 602 to be placed into the housing 604 of the feeder 600.

In some embodiments, the feeder 600 can be free-standing. In other embodiments, the feeder 600 can be mounted to an object, such as, for example, to a table. As depicted in FIG. 6A, in one embodiment, the feeder can be mounted to an articulating arm 616. The articulating arm 616 can be configured to enable the desired positioning of the feeder 600 relative to a patient's body. The articulating arm 616 can, for example, be fixedly mounted to a table, cart, chair, wall, or other suitable object. In other embodiments, the articulating arm 616 can include features to enable selective mounting to a variety of desired objects, such features including, for example, at least one clamp, at least one suction cup, at least one magnet, at least one adhesive treated area, or a variety of other affixing features.

FIG. 6A additionally depicts a control 618. The control can be configured to control aspects of the functioning of the feeder such as, for example, the feed rate. As depicted in FIG. 6A, control 618 can be located on the side 506 of the feeder 500. In other embodiments, the control 618 can be located at any of a variety of positions on or connected to the feeder 600. In some embodiments, the control can be, for example, communicatingly connected with the feeder 600. This connection can be, for example, mechanical, electrical, optical, wireless, or by any of a variety of other connections.

Figure 6B:
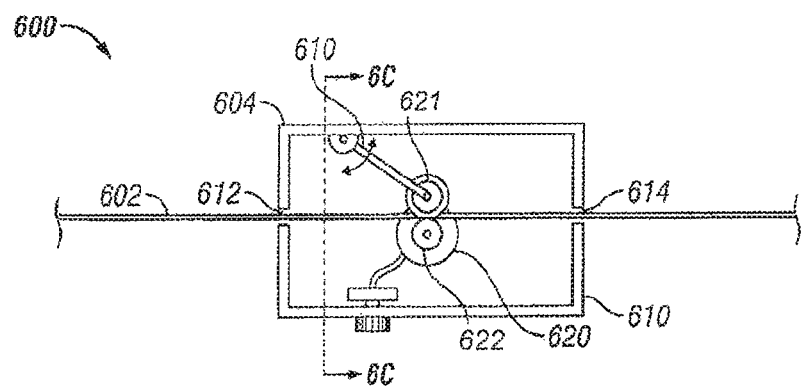
FIG. 6B illustrates a top view of one embodiment of a feeder.

FIG. 6B depicts a top view of one embodiment of a feeder 600 configured to longitudinally translate a sheath and/or wire 602. As depicted in FIG. 6B, the feeder 600 comprises a housing 604. The housing 604 depicted in FIG. 6B encloses at least a first roller 621 and a second roller 622. The rollers 621, 622 can comprise a variety of types, shapes, and sizes. In some embodiments, for example, the rollers 621, 622 can be cylindrical rollers. In other embodiments, the rollers can be, for example, spherical rollers. In some embodiments, at least one of the rollers 622 can be a drive roller. In some embodiments, the driven roller can be, for example connected to a motor directly, by gears, by a belt, or by a variety of other features. In the embodiment depicted in FIG. 6B, roller 622 is a driven roller and roller 621 is a freely rotating idler roller. A person of skill in the art will recognize that the present disclosure is not limited to the specific geometry, size, or drive characteristic of the rollers 621, 622.

The rollers 621, 622 can have different positions in different embodiments of a feeder 600. The top roller 621 and the bottom roller 622 depicted in FIG. 6B are positioned to allow a wire 602 to pass between the two rollers 621, 622. In some embodiments, the compressive force exerted by the rollers on the wire 602 can be constant or variable. In some embodiments, the relative distance between the rollers can vary to alter the compressive forces generated by the rollers 621, 622 on the wire 602. The rollers 621, 622 can additionally comprise a variety of materials. In some embodiments, the rollers can comprise natural materials, synthetic materials, polymer, composite, metal, glass, or any other material. In some embodiments, rollers 621, 622 can, for example, comprise a material selected to control the compressive force exerted by the rollers 621, 622 on the wire 602. In one embodiment, for example, the compressive force exerted by the rollers 621, 622 on the wire 602 can be controlled by making the rollers 621, 622 of a compressible material. A person of skill in the art will recognize that the present disclosure is not limited to any specific roller configuration but broadly encompasses a wide variety or rollers.

In some embodiments, the first roller 621 and/or second roller 622 can be connected to a variety of mechanisms to allow movement between positions. In one embodiment, and as depicted in FIG. 6B, first roller 621 can be located on the end of a spring loaded movable arm 610. In one embodiment, the movable arm 610 can comprise an open position in which the arm, and thereby first roller 621, is moved away from second roller 622. In this position, a wire 602 can be moved into the slots depicted in FIG. 6a and positioned between the first roller 621 and the second roller 622. The movable arm can then be moved into a second position in which the movable arm, and thereby the first roller 621, is located in proximity to the second roller 622 and thereby holds the wire 602 between the first roller 621 and the second roller 622.

In some embodiments, the sheath and/or wire 602 can comprise a tubular sheath surrounding a wire. In embodiments in which a tubular sheath surrounds a wire, the wire can connect to a first motor configured to rotably drive the wire in the vascular therapy device described above. The rollers 621, 622 can, for example, be configured to apply sufficient compressive force on the sheath to allow the rollers 621, 622 to longitudinally drive the sheath. The rollers 621, 622 can also be configured to generate insufficient compressive forces to prevent or inhibit the rotation of the wire within the sheath. This can be controlled by selection of a spring force that biases the arm 610 to engage the idler roller 621 with the driven roller 622.

The feeder 600 can control the longitudinal translation of the sheath and/or wire 602 by controlling the rotation of at least one of rollers 621, 622, which rotation feeds the sheath and/or wire 602 in the direction of the rotation of the rollers 621, 622.

Figure 6C:
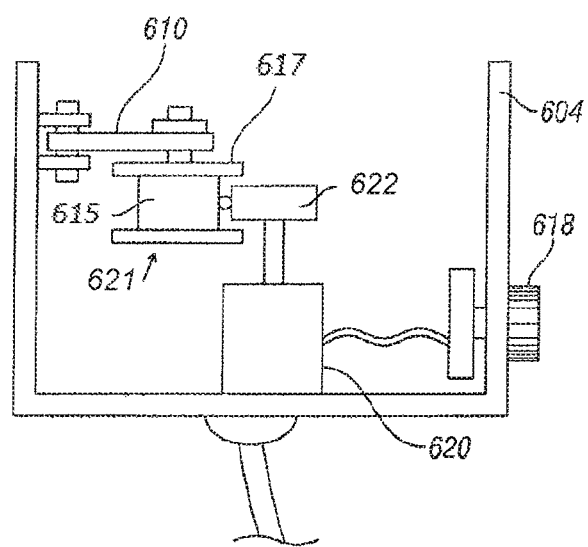
FIG. 6C illustrates a cut-away end view of one embodiment of a feeder.

FIG. 6C depicts a cut-away front view of feeder 600 depicted in FIG. 6B. FIG. 6C depicts the first roller 621 connected to the end of a movable arm 610, and the second roller 622 drivably connected to a motor 620, such as a second motor. As also depicted in FIG. 6C, first roller 621 comprises a wheel surface 615 and a flange 617. The wheel surface 615 can be configured for contacting the wire 602. The flange 617 can, in some embodiments, be configured to prevent the wire from moving out of the area between the first roller 621 and the second roller 622. As also depicted in FIG. 6C, the second motor 620 can be connected to a controller 618. Controller 618 can be configured to allow selective speed control of the motor and thereby of the rotation of the second roller 622.

When using the feeder of FIGS. 6A-6C, the physician would first place the wire/sheath into the vein of the patient, and then install a portion of the wire/sheath in the feeder and between the rollers. The damaging of the vein can be initiated by actuating the trigger on the vascular therapy device 10 described above. Before or after this actuation, the second motor 620 can be activated at the desired withdrawal speed. As the feeder pulls the wire/sheath back, the device 10 can be manually pulled back. Excess wire/sheath exiting the feeder can also drape downward somewhat, as long as no sharp bends are formed that interfere with the rotational motion of the wire within the sheath.

Based on this disclosure, a person of skill in the art will recognize that a variety of techniques and mechanisms can be configured to control and regulate the speed of longitudinal translation of a wire. A person of skill in the art will further recognize that these techniques and mechanisms can be selected for implementation based on a variety of factors including, for example, the extent of the desired wire movements, the target price of the device, and size constraints. A person of skill in the art will further recognize that the present disclosure includes a broad range of mechanisms and techniques to control the speed and a broad range of speeds of longitudinal translation of the wire.

Each of the above described embodiments can be configured to include control and feedback functionality. In some embodiments, a feeder and vascular treatment device can include, for example, wiring, at least one sensor, at least one microprocessor, at least one input capable feature, and other control or sensing components. These components can be configured to detect the speed at which the sheath and/or wire is moving and to regulate or alter that speed.

A person skilled in the art will recognize that each of these components can be inter-connected and controllably connected using a variety of techniques and hardware and that the present disclosure is not limited to any specific method of connection or connection hardware. One or more of the components depicted in the figures can, in some aspects, be excluded, and additional components can also be included, if desired.

The foregoing description details certain embodiments of the devices and methods disclosed herein. It will be appreciated, however, that no matter how detailed the foregoing appears in text, the devices and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. An apparatus for occluding a vein, comprising:
   an elongated intraluminal member shaped and dimensioned for passage through blood vessels of a subject, the intraluminal member having a proximal end and a distal end, the intraluminal member comprising:
   a sheath defining a lumen extending from the proximal end to the distal end, and a wire disposed within the lumen extending from the proximal end to the distal end, the wire being rotatable within the sheath;

a first motor coupled to the wire, the first motor configured to rotate the wire within the sheath;

an elongate track extending from a first end to a second end;

a belt coupled to the intraluminal member, the belt extending along the track from the first end to the second end; and a second motor coupled to the belt, the second motor configured to drive the belt such that the intraluminal member is withdrawn simultaneously with the first motor rotating the wire within the sheath.

2. The apparatus of claim 1, wherein the first motor is configured to rotate the wire at a rate of approximately 500-4,000 RPM.

3. The apparatus of claim 1, further comprising a loop and a hook, wherein one of the loop and the hook is coupled to the belt and the other of the loop and the hook is coupled to the intraluminal member.

4. The apparatus of claim 1, wherein the track comprises a U-shaped elongate member that extends from the first end to the second end of the track, wherein the belt runs along a bottom of the elongate member.

5. The apparatus of claim 1, wherein the track comprises at least one roller, wherein the at least one roller is coupled to the second motor and to the belt, and wherein the at least one roller is driven by the second motor.

6. An apparatus for occluding a vein, comprising:

an elongated intraluminal member shaped and dimensioned for passage through blood vessels of a subject, the intraluminal member extending from a proximal end to a distal end in a first direction, the intraluminal member comprising:
  a sheath defining a lumen extending from the proximal end to the distal end, and
  a wire disposed within the lumen extending from the proximal end to the distal end, the wire being rotatable within the sheath;

a fluid channel configured to deliver a fluid to the distal end of the elongated intraluminal member;

a first motor coupled to the wire, the first motor configured to rotate the wire within the sheath;

a roller that contacts the intraluminal member, the roller configured to rotate about a rotational axis that extends in a second direction, the second direction being substantially perpendicular to the first direction; and a second motor coupled to the roller, the second motor configured to drive the roller about the rotational axis such that the intraluminal member is withdrawn in the first direction simultaneously with the first motor rotating the wire within the sheath.

7. The apparatus of claim 6, wherein the second motor is configured to withdraw the intraluminal member at a variable rate of speed.

8. The apparatus of claim 7, wherein the second motor is configured to increase the rate of withdrawal of the intraluminal member as the intraluminal member is being withdrawn.

9. The apparatus of claim 7, wherein the second motor is configured to decrease the rate of withdrawal of the intraluminal member as the intraluminal member is being withdrawn.

10. The apparatus of claim 7, wherein the second motor is configured to withdraw the intraluminal member at a rate of approximately 1-4 mm per second.

11. The apparatus of claim 6, wherein the first motor is configured to rotate the wire at a rate of approximately 500-4,000 RPM.

12. The apparatus of claim 6, wherein the roller is a first roller and the rotational axis is a first rotational axis, the apparatus further comprising a second roller configured to contact the intraluminal member, the second roller further configured to rotate about a second rotational axis that extends in the second direction, the second rotational axis being substantially parallel to the first rotational axis.

13. The apparatus of claim 12, wherein the first roller and the second roller are positioned such that a portion of the intraluminal member is disposed between the first roller and the second roller.

14. The apparatus of claim 13, wherein the first roller and the second roller generate compressive forces on the intraluminal member.

15. The apparatus of claim 14, wherein the compressive forces inhibit the rotation of the wire within the sheath.

16. The apparatus of claim 14, wherein each of the first roller and the second roller comprises a compressible material.

17. A method for occluding a vein by damaging a vein vessel wall and applying a liquid, comprising the following steps:

advancing an elongated intraluminal member into the vein, the intraluminal member comprising a sheath defining a lumen extending from a proximal end to a distal end in a first direction, and a wire disposed within the lumen extending from the proximal end to the distal end;

rotating the wire within the sheath using a first motor, the rotating of the wire causing damage to the vein vessel wall;

simultaneously with the rotating step, withdrawing the intraluminal member using a second motor, the second motor coupled to a feeder selected from the group consisting of:
  a roller that contacts the intraluminal member, the roller configured to rotate about a rotational axis that extends in a second direction, the second direction being substantially perpendicular to the first direction, the second motor configured to drive the roller about the rotational axis such that the intraluminal member is withdrawn in the first direction simultaneously with the first motor rotating the wire within the sheath, and
  a belt coupled to the intraluminal member, the belt extending along a track, the track extending from a first end to a second end, the second motor configured to drive the belt such that the intraluminal member is withdrawn simultaneously with the first motor rotating the wire within the sheath; and injecting the liquid into the vein.

18. The method of claim 17, wherein the withdrawing step includes withdrawing the intraluminal member at a non-constant rate.

19. The method of claim 18, wherein the withdrawing step includes increasing the rate of withdrawal of the intraluminal member.

20. The method of claim 18, wherein the withdrawing step includes decreasing the rate of withdrawal of the intraluminal member.

21. The method of claim 17, wherein the withdrawing step includes withdrawing the intraluminal member at a rate of approximately 1-4 mm per second.

22. The method of claim 17, wherein the rotating step includes rotating the wire at a rate of approximately 500-4,000 RPM.

\* \* \* \* \*